United States Patent [19]

Klein et al.

[11] Patent Number: 5,440,056
[45] Date of Patent: Aug. 8, 1995

[54] 9-DEOXOTAXANE COMPOUNDS

[75] Inventors: Larry L. Klein, Lake Forest; Clinton M. Yeung, Skokie; Leping Li, Gurnee, all of Ill.

[73] Assignee: Abbott Laboratories, Abbott Park, Ill.

[21] Appl. No.: 208,509

[22] Filed: Mar. 9, 1994

Related U.S. Application Data

[63] Continuation-in-part of Ser. No. 46,678, Apr. 14, 1993, Pat. No. 5,352,806, which is a continuation-in-part of Ser. No. 914,720, Jul. 16, 1992, abandoned, which is a continuation-in-part of Ser. No. 870,509, Apr. 17, 1992, abandoned.

[51] Int. Cl.$^6$ ............................. C07D 305/14
[52] U.S. Cl. .................. 549/510; 514/449
[58] Field of Search ............... 549/510; 514/449

[56] References Cited

U.S. PATENT DOCUMENTS 4,876,399 10/1989 Holton et al. ................ 549/510

Primary Examiner—Johann Richter
Assistant Examiner—John Peabody
Attorney, Agent, or Firm—Andreas M. Danckers

[57] ABSTRACT

Compounds having the formula

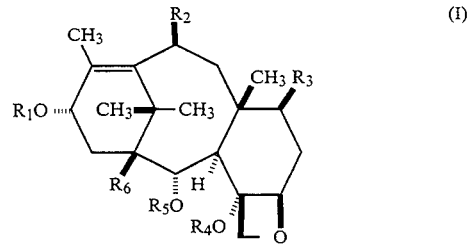

(I)

wherein —OR$^1$ comprises alkanoyl or the C-13 sidechain of taxol; R$^2$, R$^3$, and R$^6$ can be oxygenated or hydrogen in various combinations; and R$^4$ and R$^5$ are acyl groups, as well as a process for the preparation thereof, pharmaceutical compositions containing the above compounds, and a method for their use in inhibiting tumor growth.

10 Claims, No Drawings

9-DEOXOTAXANE COMPOUNDS

This application is a continuation-in-part of U.S. patent application Ser. No. 08/046,678, filed Apr. 14, 1993 now U.S. Pat. No. 5,352,806, which is a continuation-in-part of U.S. patent application Ser. No. 07/914,720, filed Jul. 16, 1992 and now abandoned, which is a continuation-in-part of U.S. patent application Ser. No. 07/870,509, filed Apr. 17, 1992 and now abandoned.

BACKGROUND OF THE INVENTION

The present invention relates to plant-derived chemotherapeutic compounds. More particularly, the invention is directed to deoxygenated taxol compounds prepared from a natural product which is isolated from *Taxus canadensis,* as well as novel analogs of taxol prepared therefrom.

Taxol, a member of the taxane family of terpenes, is of interest as a chemotherapeutic agent against a broad range of cancers. Derived primarily from the Pacific yew *Taxus brevifolia,* taxol has been shown to be active against advanced breast and ovarian cancers in clinical trials, and has exhibited promising activity against a number of other tumor types in preliminary investigations. A summary of the current state of taxol research, development and clinical testing may be found in Rotherberg, *Curr. Opin. Invest. Drugs,* 2(12):1269–1277 (1993); a review of synthetic efforts in the taxol field is provided by D.G.I. Kingston in *Prog. Chem. Org. Nat. Prod.,* 61:1–206 (1993).

Although taxol, which possesses the structural formula

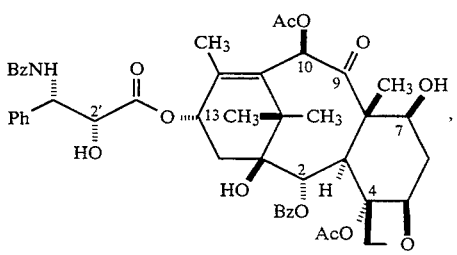

has shown considerable therapeutic potential, its scarcity in nature and the need for more potent cytostatic agents have led researchers to pursue alternative sources as well as analogs of the compound. Some efforts have been made to produce taxol in tissue and cell culture. Total chemical synthesis of the compound and its related analogs has been attempted but has not yet been achieved. The chemical conversion of naturally occurring taxol precursors such as baccatin III and cephalomannine to taxol itself or its analogs has been reported; however, additional routes for the production of potentially active taxanes are still needed.

One line of inquiry has focused on a more abundant taxane precuror, 13-acetyl-9-dihydrobaccatin III, which can be obtained from the widely distributed Canadian yew *Taxus canadensis* as described in published international application No. PCT/US93/03532, published on Oct. 28, 1993 as publication No. WO 93/21173 and incorporated herein by reference. This 9-dihydro modication makes possible the preparation of a new series of taxol analogs.

Modifications of the C-7 and C-10 positions of the baccatin moiety, including 7-deoxy, 10-desacetoxy and 7,10-dideoxytaxol derivatives, have also been described.

7-Deoxybaccatin or 7-deoxytaxol derivatives have been described in the international (PCT) application publication No. WO 93/02064, published Feb. 4, 1993 and J. Org. Chem. 58:3798–3799 (1993). 10-Desacetoxytaxol derivatives have been described in the international (PCT) application publication No. WO 93/06093, published Apr. 1, 1993; U.S. Pat. No. 5,248,796, published Sep. 28, 1993; European Patent Application EP 558959, published Sep. 8, 1993; J. Org. Chem. 58:2927–2928 (1993); and Tetrahedron Lett. 34(31):4921–24 (1993). 7,10-Dideoxytaxol derivatives have been described in J. Org. Chem. 58:5028–5029 (1993) and Tetrahedron Lett. 34(43):6845–6848 (1993).

Certain patents and patent applications also purport to generically disclose 9-deoxotaxanes, namely, U.S. Pat. Nos. 4,876,399, 5,015,744 and 5,175,315 and international (PCT) application publication No. WO 93/20036. While these disclosures refer generically to 9-deoxo compounds, they contain no teaching as to how to prepare these compounds and contain no specific examples, prophetic or actual, of 9-deoxo taxanes. Consequently, these disclosures provide no more than a motivation to attempt the preparation of such compounds.

In fact, the ability to synthesize 9-deoxygenated compounds having potentially superior biological or pharmacologic properties may offer significant advantages to the chemist and pharmacologist. It is therefore an object of the present invention to provide such compounds and the means for their preparation.

SUMMARY OF THE INVENTION

In one aspect of the present invention are disclosed 9-deoxygenated taxane compounds having the following structural formula (I):

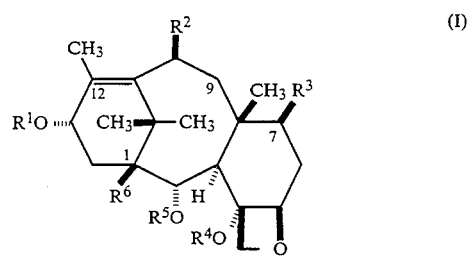

as well as prodrugs thereof. It is expected that these compounds will be useful in connection with the treatment, or in the preparation of taxol derivatives for use in treatment, of cancers and leukemias.

$R^1$ in formula (I) is alkanoyl or a radical of the formula:

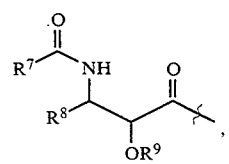

in which $R^7$ is hydrogen, alkyl, phenyl, substituted phenyl, alkoxy, substituted alkoxy, amino, substituted amino, phenoxy or substituted phenoxy; $R^8$ is hydrogen, alkyl, hydroxyalkyl, alkoxyalkyl, aminoalkyl, phenyl, substituted phenyl, α-naphthyl, or β-naphthyl; and $R^9$ is hydrogen, alkanoyl, substituted alkanoyl or aminoalkanoyl.

$R^2$, $R^3$ and $R^6$ in formula (I) are independently hydroxyl, hydrogen, alkoxyl, alkanoyloxy or aminoalkanoyloxy.

$R^4$ in formula (I) is alkyl, alkanoyl, aminoalkanoyl or aroyl.

$R^5$ in formula (I) is alkyl, alkanoyl, aminoalkanoyl or aroyl.

In a second aspect of the present invention are disclosed synthetic processes for the preparation of the above compounds, as well as novel intermediates useful therein which have the formulae:

Methyl 13-Acetyl-9-dihydrobaccatin III 9-O-xanthate;

9-Deoxobaccatin III;

13-{(2R,3S)-N-Benzyloxycarbonyl-N,O-(1-methylethylidene)-3-phenylisoserine}-9-deoxobaccatin III;

7-O-Triethylsilyl-9-deoxobaccatin III;

13-Acetyl-9-deoxobaccatin III 7-thiocarbonylimidazolide;

7-deoxy-9-deoxobaccatin III;

13-{(2R,3S)-N-Benzyloxycarbonyl-N,O-(1-methylethylidene)-3-phenylisoserine}-7-deoxy-9-deoxobaccatin III;

7-Deoxy-9-deoxobaccatin III 10-thiocarbonylimidazolide;

10-Desacetoxy-7-deoxy-9-deoxobaccatin III; and

13-{(2 R,3S)-N-Benzyloxycarbonyl-N,O-(1-methylethylidene)-3-phenylisoserine}-10-desacetoxy-7-deoxy-9-deoxobaccatin III.

Such intermediates (compounds 2, 3, 4, 8, 9, 10, 12, 13, 14 and 16) are shown in Schemes I. II and III.

DETAILED DESCRIPTION OF THE INVENTION

The compounds of the present invention compose 9-deoxotaxanes as well as derivatives thereof having the structural formula (I) wherein groups $R^1$ through $R^9$ are as described above. Specifically included among the compounds of the invention are those wherein —$R^1$ is the C-13 side-chain of taxol or a radical having the formula

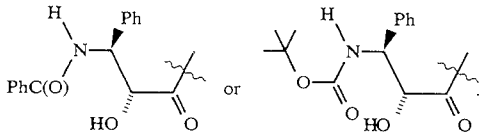

The following definitions apply to these compounds and throughout the present disclosure:

The term "alkyl" as used herein refers to a monovalent group derived by the removal of a single hydrogen atom from a straight- or branched-chain saturated hydrocarbon containing one to six carbon atoms including, but not limited to, methyl, ethyl, n- and iso-propyl, n-, sec-, iso- and tert-butyl, pentyl and hexyl.

The term "alkanoyl" as used herein refers to an alkyl function as defined above attached to the parent molecular moiety via a carbonyl group including, but not limited to, acetyl, propionyl, butanoyl and isobutanoyl.

The term "alkoxy" as used herein refers to an alkyl function as defined above attached to the parent molecular moiety via an oxygen atom including, but not limited to, methoxy, ethoxy, iso-propoxy, butoxy and tert-butoxy.

The term "alkoxyalkyl" as used herein refers to an alkoxy group, as previously defined, appended to the parent molecular moiety through an alkyl group, as previously defined.

The term "aroyl" as used herein refers to a phenyl ring attached to the parent molecular moiety through a carbonyl (—C(O)—) or thiocarbonyl group (—C(S)—). The phenyl ring may be unsubstituted or substituted with one to five substituents independently selected from halo, haloalkyl, alkyl, amino, and alkoxy.

The term "aminoalkanoyl" as used herein refers to an alkanoyl function as defined above substituted with between one and three amino groups including, but not limited to, 2-aminopropanoyl, 4-aminobutanoyl and 6-aminohexanoyl. Additionally, the amino groups optionally may be substituted with peptidyl residues of the naturally occurring amino acids, as well as di- and tripeptide residues formed therefrom.

The term "aminoalkyl" as used herein refers to an alkyl function as defined above substituted with amino or substituted amino, as defined below.

The term "halogen" as used herein refers to a substituent selected from bromo (Br), chloro (Cl), fluoro (F) and iodo (I).

The term "haloalkyl" as used herein refers to an alkyl group as defined above substituted with between one and three halogen atoms including, but not limited to, fluoromethyl, trifluoromethyl and 2-fluoroethyl.

The term "hydroxyalkyl" as used herein refers to an alkyl group as defined above substituted with a hydroxy group.

The terms "N-protected" and "N-protecting" as used herein refer to the use of a group intended to protect an amino function or the N-terminus of an amino acid or peptide against undesirable reactions during a synthetic procedure or to prevent the attack of exopeptidases on the compound or to increase the solubility of the compound and include, but are not limited to, the use in the same of such groups as sulfonyl; acyl, such as acetyl, pivaloyl and benzoyl; alkoxycarbonyl, such as tert-butyloxycarbonyl (BOC) and benzyloxycarbonyl (Cbz); and L- or D-aminoacyl residues, which may themselves be N-protected. Other examples may be found in *The Peptides*, E. Gross and J. Meienhofer, Vol. 3, Academic Press (1981), incorporated herein by reference.

The term "prodrug" as used herein refers to compounds that are rapidly transformed in vivo to yield the parent compounds of Formula (I), as for example by hydrolysis in blood. T. Higuchi and V. Stella provide a thorough discussion of the prodrug concept in "Prodrugs as Novel Delivery Systems", A.C.S. Symposium Series, Vol. 14, American Chemical Society (1975), incorporated herein by reference. Examples of esters useful as prodrugs for compounds containing carboxyl groups can be found on pages 14–21 of "Bioreversible Carriers in Drug Design: Theory and Application", ed. E. B. Roche, Pergamon Press (1987), incorporated herein by reference.

The term "prodrug ester group" as used herein refers to any of several ester-forming groups that are hydrolyzed under physiological conditions. Examples of prodrug ester groups include phosphates, pivaloyloxymethyl, acetoxymethyl, phthalidyl, indanyl and methoxymethyl, as well as other such groups known in the art.

The term "protecting group" as used herein is a term well-known in the art and refers to substituents on functional groups of compounds undergoing chemical transformation which prevent undesired reactions and degradations during a synthesis; see, for example, T. H. Greene, "Protective Groups in Organic Synthesis," John Wiley & Sons (1981), incorporated herein by reference.

The term "substituted alkanoyl" as used herein refers to an alkanoyl group as defined above substituted with between one and three groups such as hydroxyl, sulfhydryl, alkoxyl, carboxyl and halogen.

The term "substituted alkoxy" as used herein refers to an alkoxy group as defined above substituted with between one and three groups such as hydroxyl, sulfhydryl, alkoxyl, thioalkoxyl, carboxyl, amino and halogen.

The term "substituted amino" as used herein refers to an amino group substituted with one or two alkyl groups including, but not limited to, t-butylamino, benzylamino, and N,N-dimethylamino.

The term "substituted phenyl" as used herein refers to a phenyl group substituted with between one and three substituents independently selected from alkyl, halogen, haloalkyl, alkoxy, benzyloxy, thioalkoxy, hydroxy, alkanoyl, carboxy, amino, alkylamino, dialkylamino, nitro and —$OSO_3H$.

The term "substituted phenoxy" as used herein refers to a phenoxy group substituted with between one and three substituents independently selected from alkyl, halogen, haloalkyl, alkoxy, benzyloxy, thioalkoxy, hydroxy, alkanoyl, carboxy, amino, alkylamino, dialkylamino, nitro and —$OSO_3H$.

The term "thioalkoxy" as used herein refers to an alkoxy group as defined above wherein a sulfur atom is substituted for the oxygen atom.

Representative examples of the compounds of the present invention include the following:
13-Acetyl-9-deoxobaccatin III;
9-Deoxotaxol;
13-Acetyl-7-deoxy-9-deoxobaccatin III;
7- Deoxy-9-deoxotaxol;
13-Acetyl-10-desacetoxy-7-deoxy-9-deoxobaccatin III; and
10-Desacetoxy-7-deoxy-9-deoxotaxol.
Preferred among these compounds are 9-deoxotaxol, 7-deoxy-9-deoxotaxol, and 10-desacetoxy-7-deoxy-9-deoxotaxol.

Pharmaceutical compositions of the present invention comprise one or more of the above compounds in combination with a pharmaceutically acceptable carrier. By "pharmaceutically acceptable" is meant within the scope of sound medical judgement, suitable for use in contact with the tissues of humans and lower animals without undue toxicity, irritation, allergic response and the like, and are commensurate with a reasonable benefit/risk ratio. As used herein, the term "pharmaceutically acceptable carrier" means a non-toxic, inert solid, semi-solid or liquid filler, diluent, encapsulating material or formulation auxially of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other nontoxic compatible lubricants such as sodium lauryl sulfate and magnesium stearate, as well as coloring agents, releasing agents, coating agents, sweetening, flavoring and perfuming agents, preservatves and antioxidants can also be present in the composition, according to the judgement of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The methods of the present invention include a method for treating tumors in a human or lower mammal, comprising administering to a patient in need of such treatment a therapeutically effective amount of a compound of the invention, in such amounts and for such time as is necessary to achieve a therapeutic effect. By a "therapeutically effective amount" of the compound of the invention is meant a sufficient amount of the compound to treat a tumor, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, as for example from 0.001 to 50 mg/kg body weight or more usually from 0.01 to 25 mg/kg body weight. Single dose compositions may contain such amounts or submultiples thereof to make up the daily dose. In general, treatment regimens according to the present invention compose administration to a human patient in need of such treatment from about 10 mg to about 1000 mg of the compound(s) of this invention per day in single or multiple doses.

More generally, the methods of the present invention include the inhibition of growth of a mammalian tumor by exposing the tumor to a compound of the invention, in such concentration and for such time as is necessary to obtain the desired inhibition.

The processes of the present invention, in which the above compounds of formula (I) are prepared from 9-dihydro-13-acetylbaccatin III (compound 1), comprise the steps of:
- (a) thioacylating 9-dihydro-13-acetylbaccatin III to give a 9-thioacyl compound;
- (b) deoxygenating the product of step (a);
- (c) deacetylating in the 13-position;
- (d) adding a suitable side-chain to the C-13 position of the product of step (c); and
- (e) selectively deprotecting of the product of step (d).

A process for preparing a 7-deoxy-9-deoxotaxane compound comprises the steps of:
- (a) thioacylating 9-dihydro-13-acetylbaccatin III to give a 9-thioacyl compound;
- (b) deoxygenating the product of step (a);
- (c) repeating steps (a) and (b) in the 7-position;
- (d) deacetylating in the 13-position;
- (e) adding a suitable side-chain to the C-13 position of the product of step (d); and
- (f) selectively deprotecting of the product of step (e).

A process for preparing a 7-dexoy9-deoxo-10-desacetoxytaxane compound comprises the steps of:
- (a) thioacylating 9-dihydro-13-acetylbaccatin III to give a 9-thioacyl compound;
- (b) deoxygenating the product of step (a);

(c) repeating steps (a) and (b) in the 7-position;
(d) deacetylating in the 10-position;
(e) repeating steps (a) and (b) in the 10-position;
(f) deacetylating in the 13-position;
(g) adding a suitable side-chain to the C-13 position of the product of step (f); and
(h) selectively deprotecting of the product of step (g).

More specifically, it has been found that compound 1 of the present invention may be obtained by alcoholic extraction from crushed needles and twigs of *Taxus canadensis*. This extract is then purified using customary separatory techniques, beginning with partitioning between solvent systems consisting of acetone, methanol, hexane, heptane and water to remove fats and lipids. The defatted crude extract is further partitioned, in several stages, between solvent systems consisting of methanol, methylene chloride, chloroform, ethyl acetate and water. Those fractions of the extract which are soluble in a solvent system consisting either of methylene chloride or of chloroform and ethyl acetate contain compound 1.

The above fractions may be further purified by planet coil countercurrent chromatography (PCCC), using solvent systems consisting of hexane, methanol, methylene chloride, chloroform, toluene, and water or suitable aqueous buffers. The various fractions contain several taxane derivatives, including taxol, cephalomannine and baccatin III. The solvent is removed from the fraction containing compound 1, which is recrystallized from methanol or ethanol and water to afford the pure compound as white crystals. If desired, taxol, baccatin, and other related compounds may also be isolated from the various chromatographic fractions.

Asymmetric centers may exist in the compounds of the present invention. The present invention contemplates the various stereoisomers and mixtures thereof. Starting compounds of particular stereochemistry are either commercially available or are made by the methods detailed below and resolved by techniques well known in the organic chemical arts.

In general, the compounds of formula (I) may then be synthesized from compound 1 by treatment with a thioacylating agent at C-9, followed by tin hydride reduction to give compounds shown in Scheme I. Further thioacyl/reduction steps can be carried out on 3 for the other hydroxyls at C-7, C-10 and C-1, as for 9, 14, etc. These deoxy compounds can also be deacetylated at C-13 as for 10 and 12; the C-13 hydroxyl treated as above with lactams or acetonide forms of the appropriate side chain; the side chain protecting groups removed; and the side chain nitrogen acylated to afford the final 9-deoxo analogs.

As a particular example of the process illustrated below in Scheme I, 13-acetyl-9-dihydrobaccatin III (1) is treated with lithium hexamethyldisilazide, carbon disulfide, and methyl iodide to give the C-9 methyl xanthate 2. Compound 2 is treated with tributyltin or tris(trimethylsilyl)silane or other trisubstituted tin agents to effect a deoxygenation giving compound 3, followed by methyllithium to remove the acetyl group in the 13-position giving compound 4, which is shown with a hydroxy-protecting group in the 7-position. Compound 4 is then reacted with an appropriate protected side-chain derivative (as for example (3R,4S)-N-acyl-3-O-(1-ethoxyethyl)-4-phenyl-2-azetidinone (5) or (2R,3S)-N-protected-N,O-(1-methylethylidene)-3-phenylisoserine (6)). The protecting groups may then be removed with a mild acid when intermediate 5 is used, as for example 1% HCl in ethanol or methanol, or catalytically hydrogenated when intermediate 6 is used. When intermediate 6 is used, deprotection is followed 3'-aminoacylation (as for example treatment with benzoic anhydride) to produce the desired 9-deoxotaxanes of formula (I), in this case, 9-deoxotaxol (7). (When intermediate 5 is used, R is the desired acyl group, i.e. benzoyl in the case of the taxol analogs.) Alternatively, the deoxygenation steps can be repeated on compound 3 to give the 9-deoxo-7-deoxy compound 9.

The further elaboration of compound 9 is shown in Scheme II. Treatment of compound 9 with methyllithium to remove the 13-acetyl protecting group gives compound 10. Compound 10 may then be reacted with an appropriate protected side-chain derivative (as for example (3R,4S)-N-acyl-3-O-(1-ethoxyethyl)-4-phenyl-2-azetidinone (5), or (2R,3S)-N-protected-N,O-(1-methylethylidene)-3-phenylisoserine (6)). The protecting groups are then removed with a mild acid (as for example 1% HCl in ethanol or methanol) when compound 5 is used or hydrogenated when compound 6 is used. When intermediate 6 is used, deprotection is followed 3'-aminoacylation to produce the desired 9-deoxo-7-deoxytaxanes of formula (I). When benzoic anhydride is used, 9-deoxo-7-deoxytaxol (11) is afforded. (When intermediate 5 is used, R is the desired acyl group, i.e. benzoyl in the case of the taxol analogs.)

Alternatively, the 13-acetyl protecting group is removed (as for example with methyllithium) to give compound 12. The deoxygenation steps can be repeated on compound 12 to give the 9-deoxo-7,10-dideoxy compound 14. Compound 14 may then be reacted with an appropriate protected side-chain derivative (for example, (3R,4S)-N-acyl-3-O-(1-ethoxyethyl)-4-phenyl-2-azetidinone (5) or (2R,3S)-N-acyl-N,O-(1-methylethylidene)-3-phenylisoserine (6)). The protecting groups are then removed with a mild acid (for example 1% HCl in ethanol or methanol) when compound 5 is used or hydrogenated when compound 6 is used. When intermediate 6 is used, deprotection is followed 3'-aminoacylation to produce the desired 9-deoxo-7,10-dideoxytaxanes of formula (I). When benzoic anhydride is used as the acylating agent, 9-deoxo-7-deoxy-10-desacetoxytaxol (15) results. (When intermediate 5 is used, R is the desired acyl group of the final product, i.e. benzoyl in the case of the taxol analogs.)

Scheme III illustrates the use of intermediate 6 ((2R,3S)-N-protected-N,O-(1-methylethylidene)-3-phenylisoserine) in the preparation of 9-deoxo-7-deoxy-10-desacetoxytaxol. The deoxygenated 13-deacetylated baccatin III (14) is reacted with side chain precursor 6, where R* is a nitrogen protecting group such as benzyloxycarbonyl, to give compound 16. The nitrogen protecting group is removed (as for example by catalytic hydrogenation when R* is benzyloxycarbonyl) and then the side chain amino group is acylated (as for example with benzoic anhydride) to give the final product (15).

It will be appreciated by one skilled in the art that the deoxygenations and the selective protection and deprotection steps affecting the several hydroxyl groups on the baccatin III structure may be carried out in varying order or number of steps, as necessary, and that Schemes I and II are intended to encompass such variations.

Scheme I
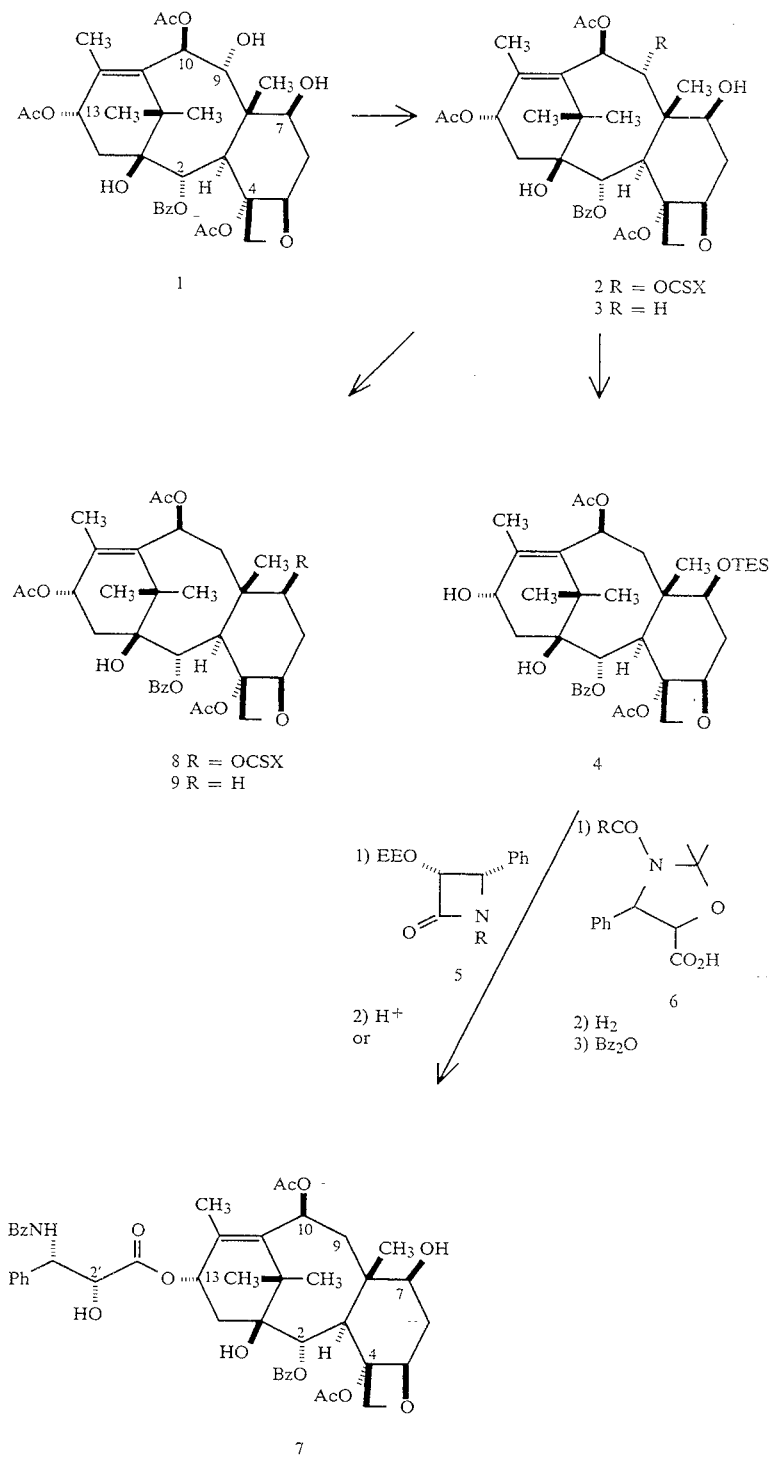

Scheme II
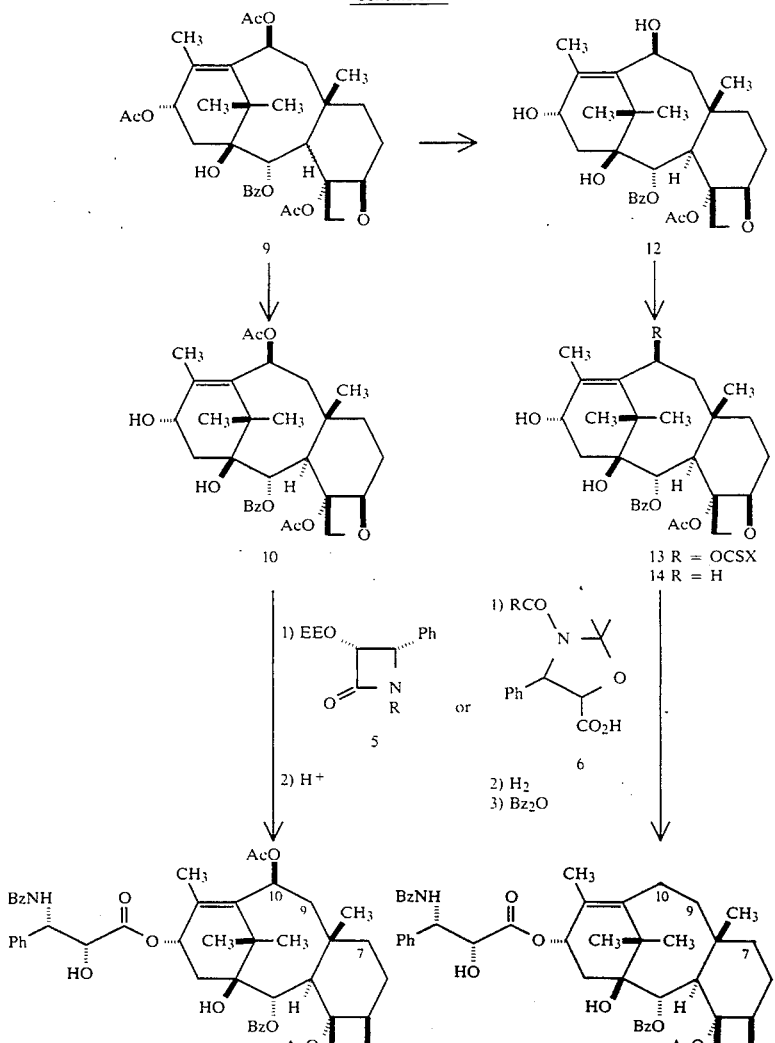
Scheme III
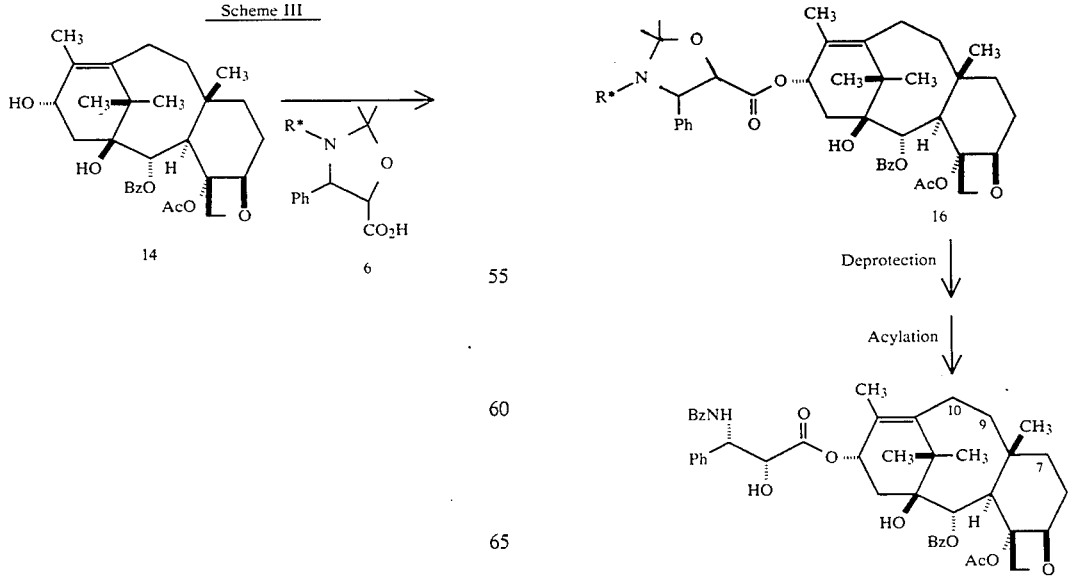

The foregoing may be better understood by reference to the following Examples, in which particular reagents and conditions utilized in these syntheses are described in detail. These Examples are provided for purposes of illustration and are not intended as a limitation upon the invention. The following abbreviations are used: AIBN for 2,2'-azobis-(2-methylpropionitrile), $CH_2Cl_2$ for methylene chloride, DMAP for dimethylaminopyridine, DMF for dimethylformamaide, EtOAc for ethyl acetate, LHMDS for lithium hexamethyldisilazide, MeOH for methanol, and THF for tetrahydrofuran.

EXAMPLE 1

Methyl 13-Acetyl-9-dihydrobaccatin III 9-O-xanthate (Scheme I, Compound (2))

To 13-acetyl-9-dihydrobaccatin III (1) (1 g, 1.58 mmol) dissolved in THF (100 mL) at −25 °C. under nitrogen was added LHMDS (3.5 mL, 1M in THF, 3.5 mmol) followed after 15 minutes by carbon disulfide (0.33 mL, 5.2 mmol) and after 5 minutes by methyl iodide (0.33 mL, 5.2 mmol). After 1 hour the reaction was complete by thin layer chromatographic analysis. The reaction was quenched by the addition of pH 7 phosphate buffer and the organic layer was combined with ethyl acetate and separated, dried, and evaporated in vacuo. The residue was purified by silica gel column chromatography using 97:3 $CHCl_3$-MeOH to give 0.66 g (58%) of methyl 13-acetyl-9-dihydrobaccatin III 9-O-xanthate (2). $^1H$ NMR ($CDCl_3$, 300 MHz) δ 8.1 (d, 2H, ArH), 7.62 (t, 1H, ArH), 7.49 (t, 2H, ArH), 6.88 (d, 1H, H-9), 6.43 (d, 1H, H-10), 6.18 (t, 1H, H-13), 5.92 (d, 1H, H-2), 4.99 (d, 1H, H-5), 4.45 (t, 1H, H-7), 4.32 (d, 1H, H-20$_a$), 4.19 (d, 1H, H-20$_b$), 3.1 (d, 1 H, H-3), 2.7-2.6 (m, 1H, H-6$_a$), 2.63 (s, 3H, SMe), 2.3 (s, 3H, OAc), 2.22 (d, 1H, H-14$_a$), 2.2 (s, 3H, OAc), 2.01 (s, 3H, OAc), 1.99 (d, 3H, vinyl-$CH_3$), 2.05-1.8 (m, 2H, H-6$_b$, H-14$_b$), 1.84 (s, 3H, $CH_3$), 1.61 (s, 3H, $CH_3$), 1.25 (s, 3H, $CH_3$). MS (DCl/$NH_3$) m/e 738 (M+H+$NH_3$)$^+$.

EXAMPLE 2

13-Acetyl-9-deoxobaccatin III (Scheme I, Compound (3))

To a solution of the compound resulting from Example 1 (0.66 g, 0.92 mmol) and 2,2'-azobis(2-methylpropionitrile) (AIBN, 30 mg) in toluene (20 mL) stirred at 100° C. under nitrogen was added dropwise tri-n-butyltin hydride (0.3 mL, 1.12 mmol). After 30 minutes the reaction was complete by thin layer chromatographic analysis. The reaction was quenched by the addition of pH 7 phosphate buffer, and the organic layer was combined with ethyl acetate and separated, dried, and evaporated in vacuo. The residue was purified by silica gel column chromatography eluting with 95:5 $CHCl_3$-MeOH to give 0.535 g (95%) of the title compound (3). $^1H$ NMR ($CDCl_3$, 300 MHz) δ 8.1 (d, 2H, ArH), 7.61 (t, 1H, ArH), 7.48 (t, 2H, ArH), 6.17 (t, 1H, H-13), 5.93 (d, 1H, H-10), 5.77 (d, 1H, H-2), 4.97 (d, 1H, H-5), 4.29 (d, 1H, H-20$_a$), 4.13 (d, 1H, H-20$_b$), 4.04 (t, 1H, H-7), 3.03 (d, 1 H, H-3), 2.58 (ddd, 1H, H-6$_a$), 2.38 (brs, 1 H, H-7OH), 2.31-2.26 (m, 2H, H9), 2.27 (s, 3H, 4-OAc), 2.23-2.19 (m, 2H-14), 2.19 (s, 3H, 13-OAc), 2.09 (s, 3H, 10-OAc), 1.85 (d, 3H, vinyl-$CH_3$), 1.88-1.8 (m, 1H, H-6$_b$), 1.72 (s, 3H, $CH_3$), 1.4 (s, 3H, 19-$CH_3$), 1.26 (s, 3H, $CH_3$).

EXAMPLE 3

9-Deoxobaccatin III

To a solution of the compound resulting from Example 2 (0.188 g, 1.37 mmol) in THF (40 mL) stirred under nitrogen at −78° C. was added methyllithium (1.4M in ether, 1 mL, 6.2 mmol) dropwise. After 45 minutes the reaction was complete by thin layer chromatographic analysis. The reaction was quenched by adding into 400 mL pH 7 phosphate buffer and ethyl acetate, and the organic layer was separated, dried, and evaporated in vacuo. The residue was purified by silica gel column chromatography eluting with 95:5 $CHCl_3$-MeOH to give 70 mg (40%) of the title compound (4). $^1H$ NMR ($CDCl_3$, 300 MHz) δ 8.13 (d, 2H, ArH), 7.61 (t, 1H, ArH), 7.48 (t, 2H, ArH), 5.9 (dd, 1H, H-10), 5.73 (d, 1H, H-2), 4.95 (d, 1H, H-5), 4.8 (m, 1H, H-13), 4.3 (d, 1H, H-20$_a$), 4.14 (d, 1H, H-20$_b$), 4.07 (dd, 1H, H-7), 3.1 (d, 1H, H-3), 2.68 (ddd, 1H, H-6$_a$), 2.35-2.0 (m, 4H, H9, H14), 2.27 (s, 3H, OAc), 2.1 (s, 3H, OAc), 2.01 (d, 3H, vinyl-$CH_3$), 1.83 (ddd, 1 H, H-6$_b$), 1.69 (s, 3H, $CH_3$), 1.4 (s, 3H, 19-$CH_3$), 1.26 (s, 3H, $CH_3$). MS (DCl/$NH_3$) m/e 573 (M+H)$^+$, 590 (M+H+$NH_3$)$^+$.

EXAMPLE 4

7-O-Triethylsilyl-9-deoxobaccatin III (Scheme I, Compound (4))

The compound resulting from Example 3 (4) (70 mg, 0.12 mmol) was combined with triethylamine (0.2 mL, 1.43 mmol), 4-dimethylaminopyridine (DMAP, 5 mg) and triethylsilyl chloride (0.1 mL, 0.58 mmol) in $CHCl_3$ (1 mL) at 25° C. After three hours the mixture was quenched with buffer and ethyl acetate. The organic extract was washed, dried, and concentrated in vacuo to afford a residue which was purified by silica gel column chromatography eluting with 97:3 $CHCl_3$-MeOH to give 76 mg (90%) of the title compound (4). $^1H$ NMR ($CDCl_3$, 300 MHz) δ 8.13 (d, 2H, ArH), 7.61 (t, 1H, ArH), 7.48 (t, 2H, ArH), 5.82 (dd, 1H, H-10), 5.75 (d, 1H, H-2), 4.9 (d, 1H, H-5), 4.77 (m, 1H, H-13), 4.3 (d, 1H, H-20$_a$), 4.14 (d, 1H, H-20$_b$), 4.02 (dd, 1H, H-7), 3.13 (d, 1H, H-3), 2.51 (ddd, 1H, H-6$_a$), 2.45-2.0 (m, 4H, H9, H14), 2.27 (s, 3H, OAc), 2.13 (d, 3H, vinyl-$CH_3$), 2.05 (s, 3H, OAc), 1.85 (ddd, 1H, H-6$_b$), 1.67 (s, 3H, $CH_3$), 1.4 (s, 3H, 19-$CH_3$), 1.18 (s, 3H, $CH_3$), 0.99 (t, 9H, Si-C-$CH_3$), 0.6-0.7 (m, 6H, Si-$CH_2$). MS (DCl/$NH_3$) m/e 686 (M+H)$^+$.

EXAMPLE 5

9-Deoxotaxol (Scheme I, Compound (7))

To a solution of the compound resulting from Example 4, 7-O-triethylsilyl-9-deoxobaccatin III, (45 mg, 0.06 mmol) in THF at 25° C. was added sodium hydride (60% by wt., 40 mg, 0.9 mmol), followed by (3R,4S)-N-benzoyl-3-O-(1-ethoxyethyl)-4-phenyl-2-azetidinone (compound 5), prepared as described by Georg et al., *Bioorganic & Medicinal Chemistry Letters* 2(4):295 (1992) or Ojima et al., *J. Org. Chem.* 56:1681 (1991) [each incorporated herein by reference], (133 mg, 0.36 mmol). After 7 hours the reaction was complete by thin layer chromatographic analysis. The mixture was quenched with buffer and ethyl acetate. The organic extract was washed, dried, and concentrated in vacuo to afford a residue which was directly combined with 1% HCl in methanol (2 mL) at 25° C. After stirring for 2 hours the reaction was complete by thin layer chromatographic analysis and quenched with buffer and ethyl acetate. The organic extract was washed, dried, and concentrated in vacuo prior to purification by preparative thin layer chromatography (0.5 mm) with 93:7 CHCl$_3$-MeOH to give 17 mg (30%) of the title compound. $^1$H NMR (CDCl$_3$, 300 MHz) δ 8.09 (d, 2H, ArH), 7.82 (d, 2H, ArH), 7.61 (t, 1 H, ArH), 7.55-7.3 (m, 11H, ArH, NH), 6.1 (t, 1H, H-13), 5.86 (m, 2H, H-10, H-3'), 5.78 (d, 1H, H-2), 4.93 (d, 1H, H-5), 4.75 (t, 1H, H-2'), 4.39 (d, 1H, 2'-OH), 4.29 (d, 1H, H-20$_a$), 4.15 (d, 1H, H-20$_b$), 3.94 (br t, 1H, H-7), 2.99 (d, 1H, H-3), 2.58 (m, 1H), 2.37 (dd,1H), 2.29 (s, 3H, OAc), 2.1 (s, 3H, OAc), 2.3-1.5 (m, 7H), 1.7 (d, 3H, vinyl-CH$_3$), 1.6 (s, 3H, CH$_3$), 1.4 (s, 3H, CH$_3$), 1.2 (s, 3H, CH$_3$). MS (FAB/K$^+$) m/e 878 (M+K)$^+$.

EXAMPLE 6

13-Acetyl-9-deoxobaccatin III 7-thiocarbonylimidazolide (Scheme I, Compound (8))

A solution of the compound resulting from Example 2, 13-acetyl-9-deoxobaccatin III, (0.78 g, 1.27 mmol), thiocarbonyl diimidazolide (0.5 g, 2.8 mmol), and DMAP (20 mg) in toluene (5 mL) was heated to 100° C. After 3 hours the reaction was complete by thin layer chromatographic analysis. The mixture was quenched with buffer and ethyl acetate. The organic extract was washed, dried, and concentrated in vacuo prior to purification by silica gel column chromatography with 97:3 CHCl$_3$-MeOH to give 0.81 g (88%) of the title compound. $^1$H NMR (CDCl$_3$, 300 MHz) δ 8.4 (br s, 1 H, imid.), 8.1 (d, 2H, ArH), 7.67 (br s, 1H, imid.), 7.62 (t, 1H, ArH), 7.5 (t, 2H, ArH), 7.1 (br s, 1H, imid.), 6.19 (t, 1H, H-13), 5.94 (dd, 1H, H-7), 5.86 (dd, 1H, H-10), 5.82 (d, 1H, H-2), 5.0 (d, 1H, H-5), 4.38 (d, 1H, H-20$_a$), 4.19 (d, 1H, H-20$_b$), 3.27 (d, 1H, H-3), 2.95 (ddd, 1H, H-6$_a$), 2.32 (s, 3H, OAc), 2.21 (s, 3H, OAc), 2.0-2.45 (m, 5H), 1.94 (s, 3H, OAc), 1.91 (d, 3H, vinyl-CH$_3$), 1.71 (m, 1 H,), 1.7 (s, 3H, CH$_3$), 1.69 (s, 3H, CH$_3$), 1.25 (s, 3H, CH$_3$). MS (DCl/NH$_3$) m/e 725 (M+H)$^+$.

EXAMPLE 7

13-Acetyl-7-deoxy-9-deoxobaccatin III (Scheme II, Compound (9))

To a solution of the compound resulting from Example 6 (0.81 g, 1.12 mmol) and AIBN (20 mg) in toluene (20 mL) stirred at 100° C. under nitrogen was added dropwise tri-n-butyltin hydride (0.33 mL, 1.23 mmol). After 15 minutes the reaction was complete by thin layer chromatographic analysis. The mixture was quenched with buffer and ethyl acetate. The organic extract was washed, dried, and concentrated in vacuo prior to purification by silica gel column chromatography with 98:2 CHCl$_3$-MeOH to give 0.63 g (94%) of the title compound. $^1$H NMR (CDCl$_3$, 300 MHz) δ 8.1 (d, 2H, ArH), 7.6 (t, 1H, ArH), 7.49 (t, 2H, ArH), 6.15 (t, 1H, H-13), 6.05 (dd, 1H, H-10), 5.72 (d, 1H, H-2), 4.9 (d, 1H, H-5), 4.3 (d, 1H, H-20$_a$), 4.1 (d, 1H, H-20$_b$), 3.07 (d, 1H, H-3), 2.6 (dd, 1H, H-6$_a$), 2.29 (s, 3H, OAc), 2.22-1.2 (m, 11H), 2.2 (s, 3H, OAc), 2.07 (s, 3H, OAc), 1.9 (d, 3H, vinyl-CH$_3$), 1.7 (s, 3H, CH$_3$), 1.46 (s, 3H, CH$_3$), 1.22 (s, 3H, CH$_3$). MS (DCl/NH$_3$) m/e 599 (M+H)$^+$, 616 (M+H+NH$_3$)$^+$.

EXAMPLE 8

7-Deoxy-9-deoxobaccatin III (Scheme II, Compound (10))

To a solution of the compound resulting from Example 7 (0.817 g, 1.36 mmol) in THF (140 mL) stirred under nitrogen at −78° C. was added methyllithium (1.4M in ether, 2.44 mL, 3.4 mmol) dropwise. After 2 hours the reaction was complete by thin layer chromatographic analysis. The reaction was quenched by adding the mixture into pH 7 phosphate buffer (400 mL) and ethyl acetate, and the organic layer was separated, dried, and evaporated in vacuo. The residue was purified by silica gel column chromatography eluting with 96:4 CHCl$_3$-MeOH to give 0.21 g (27%) of 7-deoxy-9-deoxobaccatin III (10) and 0.22 g (31%) of 10-deacetyl-7-deoxy-9-deoxobaccatin III (12). $^1$H NMR (CDCl$_3$) δ8.1 (d, 2H, ArH), 7.6 (t, 1 H, ArH), 7.48 (t, 2H, ArH), 6.02 (dd, 1H, H-10), 5.7 (d, 1H, H-2), 4.94 (d, 1H, H-5), 4.77 (brt, 1H, H-13), 4.3 (d, 1H, H-20$_a$), 4.13 (d, 1H, H-20$_b$), 3.12 (d, 1H, H-3), 2.58 (dd, 1H, H-6$_a$), 2.27 (s, 3H, OAc), 2.35-1.5 (m, 9H), 2.08 (s 3H, OAc), 2.07 (s, 3H, vinyl-CH$_3$), 1.65 (s, 3H, CH$_3$), 1.46 (s, 3H, CH$_3$), 1.08 (s, 3H, CH$_3$). MS (DCl/NH$_3$) m/e 557 (M+H)$^+$, 574 (M+H+NH$_3$)$^+$.

EXAMPLE 9

7-Deoxy-9-deoxotaxol (Scheme II, Compound (11))

To a solution of 7-deoxy-9-deoxobaccatin III (10) (24 mg, 0.043 mmol) in THF (1 mL) at 25° C. was added sodium hydride (60% by wt. 20 mg, 0.46 mmol), followed by (3R,4S)-N-benzoyl-3-O-(1-ethoxyethyl)-4-phenyl-2-azetidinone (compound 5), prepared as described by Georg et al, *Bioorganic & Medicinal Chemistry Letters* 2(4):295 (1992) or Ojima et al., *J. Org. Chem.* 56:1681 (1991), (48 mg, 0.141 mmol). After 24 hours the reaction was complete by thin layer chromatographic analysis. The mixture was quenched by adding it into buffer (200 mL) and ethyl acetate. The organic extract was washed, dried, and concentrated in vacuo to afford a residue which was directly combined with 1% HCl in methanol (1 mL) at 25° C. After stirring for 3 hours the reaction was complete by thin layer chromatographic analysis and quenched with buffer and ethyl acetate. The organic extract was washed, dried, and concentrated in vacuo prior to purification by preparative thin layer chromatography (0.25 mm) with 97:3 CHCl$_3$-MeOH to give 5.76 mg (16.2%) of the title compound. $^1$H NMR (CDCl$_3$, 300 MHz) δ 8.13 (d, 2H, ArH), 7.82 (d, 2H, ArH), 7.61 (t, 1H, ArH), 7.53-7.25 (m, 11H, ArH, NH), 6.1 (t, 1H, H-13), 5.98 (dd, 1H, H-10), 5.83 (dd, 1H, H-3'), 5.85 (d, 1H, H-2), 4.96 (d, 1H, H-5), 4.77 (d, 1H, H-2'), 4.42 (br s, 1H, OH), 4.3 (d, 1H, H-20$_a$), 4.15 (d, 1H, H-20$_b$), 3.03 (d, 1H, H-3), 2.58 (dd, 1H), 2.37 (dd,1H), 2.3 (s, 3H, OAc), 2.25-1.5 (m, 7H), 2.05 (s, 3H, OAc), 1.7 (d, 3H, vinyl-CH$_3$), 1.67 (s, 3H, CH$_3$), 1.48 (s, 3H, CH$_3$), 1.19 (s, 3H, CH$_3$). MS (FAB/K$^+$) m/e 862 (M+K)$^+$.

EXAMPLE 10

7-Deoxy-9-deoxobaccatin III 10-thiocarbonylimidazolide (Scheme II, Compound (13))

A solution of 10-deacetyl-7-deoxy-9-deoxobaccatin III (12), resulting from Example 8, (165 mg, 0.32 mmol), thiocarbonyl diimidazolide (114 mg, 0.64 mmol), and DMAP (16 mg) in 3 mL of toluene was heated to 82° C. After 1 hour the reaction was complete by thin layer chromatographic analysis. The mixture was quenched with buffer and ethyl acetate. The organic extract was washed, dried, and concentrated in vacuo prior to purification by silica gel column chromatography with 96:4 $CHCl_3$-MeOH to give 180 mg (90%) of the title compound. $^1H$ NMR ($CDCl_3$, 300 MHz), δ 8.25 (br s, 1H, imid.), 8.12 (d, 2H, ArH), 7.61 (t, 1H, ArH), 7.5 (t, 2H, ArH), 7.49 (br s, 1H, imid.), 7.13 (br s, 1H, imid.), 5.71 (d, 1H, H-2), 5.34 (dd, 1H, H-10), 4.97 (d, 1H, H-5), 4.8 (t, 1H, H-13), 4.32 (d, 1H, H-$20_a$), 4.13 (d, 1H, H-$20_b$), 3.23 (d, 1H, H-3), 2.8 (ddd, 1H), 2.29 (s, 3H, OAc), 2.4-1.6 (m, 9H), 2.05 (s, 3H, vinyl-$CH_3$), 1.65 (s, 3H, $CH_3$), 1.48 (s, 3H, $CH_3$), 1.15 (s, 3H, $CH_3$). MS ($DCl/NH_3$) m/e 625 $(M+H)^+$.

EXAMPLE 11

10-Desacetoxy-7-deoxy-9-deoxobaccatin III (Scheme II, Compound (14))

To a solution of the compound resulting from Example 10 (180 mg, 0.28 mmol) and AIBN (25 mg) in toluene (5 mL) stirred at 100° C. under nitrogen was added dropwise tri-n-butyltin hydride (0.28 mL, 1 mmol). After 1 hour the reaction was complete by thin layer chromatographic analysis. The mixture was quenched with buffer and ethyl acetate. The organic extract was washed, dried, and concentrated in vacuo prior to purification by silica gel column chromatography with 95:5 $CHCl_3$-MeOH to give 102 mg (71%) of the title compound. $^1H$ NMR ($CDCl_3$, 300 MHz) δ 8.14 (d, 2H, ArH), 7.6 (t, 1 H, ArH), 7.48 (t, 2H, ArH), 5.72 (d, 1H, H-2), 4.94 (d, 1H, H-5), 4.73 (br q, 1H, H-13), 4.32 (d, 1H, H-$20_a$), 4.16 (d, 1H, H-$20_b$), 3.35 (d, 1H, H-3), 2.79 (dd, 1H), 2.3 (s, 3H, OAc), 2.35-1.5 (m, 9H), 1.9 (s, 3H, vinyl-$CH_3$), 1.5 (s, 3H, $CH_3$), 1.41 (s, 3H, $CH_3$), 1.1 (s, 3H, $CH_3$). MS ($DCl/NH_3$) m/e 499 $(M+H)^+$.

EXAMPLE 12

13-{(2R,3S)-N-Benzyloxycarbonyl-N,O-(1-methylethylidene)-3-phenylisoserine}-10-desacetoxy-7-deoxy-9-deoxotaxol (Scheme II, Compound (16) where R is Benzyloxycarbonyl)

A solution of the compound resulting from Example 11 (20 mg, 0.04 mmol), DMAP (9.8 mg, 0.08 mmol), dicyclohexylcarbodiimide (32 mg, 0.15 mmol), and (2R,3S)-N-benzyloxycarbonyl-N,O-(1-methylethylidene)-3-phenylisoserine, prepared in a manner analogous to the procedure of Commercon, A., Bezard, D., Bernard, F., Bourzat, J. D. Tetrahedron Lett., 33: 5185 (1992) [incorporated herein by reference] for (2R,3S)-N-Boc-N,O-(1-methylethylidene)-3-phenylisoserine, (48 mg, 0.13 mmol) in toluene (2 mL) heated at 80° C. under nitrogen for 3 hours. The mixture was quenched with buffer and $CHCl_3$. The organic extract was washed, dried, and concentrated in vacuo prior to purification by silica gel column chromatography with 60:40 hexane-EtOAc to give 10 mg (30%) of the title compound. $^1H$ NMR ($CDCl_3$, 300 MHz) δ 8.07 (d, 2H, ArH), 7.6 (t, 1 H, ArH), 7.46 (t, 2H, ArH), 7.4-7.1 (m, 10H, ArH), 6.8 (br s, 1H, H-3'), 6.17 (t, 1H, H-13), 5.87 (dd, 1H), 5.7 (d, 1H, H-2), 5.24 (br d, 1H, H-3'), 5.1-4.8 (br s, 2H, $ArCH_2$), 4.91 (d, 1H, H-5), 4.88 4.55 (d, 1H, H-2'), 4.25 (d, 1H, H-$20_a$), 4.08 (d, 1H, H-$20_b$), 3.21 (d, 1H, H-3), 2.82 (m, 1H), 2.25-1.4 (m, 7H), 1.77 (s, 6H), 1.55 (s, 6H), 1.39 (s, 3H), 1.23 (s, 3H). MS ($DCl/NH_3$) m/e 836 $(M+H)^+$, 853 $(M+NH_4)^+$.

EXAMPLE 13

10-Desacetoxy-7-deoxy-9-deoxotaxol (Scheme II, Compound (15))

A suspension of the compound resulting from Example 12 (5 mg, 0.006 mmol) and 10% Pd/C (10 mg) in 30% MeOH/water was subjected to balloon hydrogenolysis for 1.5 hours. The reaction mixture was filtered and benzoic anhydride (6 mg, 0.026 mmol) was added. After stirring for 3 hours the reaction was complete by thin layer chromatographic analysis and quenched with buffer and $CHCl_3$. The organic extract was washed, dried, and concentrated in vacuo prior to purification by preparative thin layer chromatography (0.25 mm) with 95:5 $CHCl_3$-MeOH to give 1.6 mg (35 %) of the title compound. $^1H$ NMR ($CDCl_3$, 300 MHz) δ 8.1 (d, 2H, ArH), 7.85 (d, 2H, ArH), 7.6 (t, 1 H, ArH), 7.55-7.25 (m, 11H, ArH, NH), 6.05 (t, 1H, H-13), 5.87 (dd, 1H, H-3'), 5.76 (d, 1H, H-2). 4.98 (d, 1H, H-5), 4.88 (br s, 1H, H-2'-OH), 4.74 (d, 1H, H-2'), 4.3 (d, 1H, H-$20_a$), 4.17 (d, 1H, H-$20_b$), 3.14 (d, 1H, H-3), 2.68 (m, 1H), 2.4-1.5 (m, 9H), 2.29 (s, 3H, OAc), 1.5 (s, 3H, vinyl-$CH_3$), 1.43 (s, 3H, $CH_3$), 1.4 (s, 3H, $CH_3$), 1.13 (s, 3H, $CH_3$).

EXAMPLE 14

Assay for In Vitro Tumor Cell Cytotoxicity

The compounds of the present invention were tested for in vitro cytotoxic activity against the tumor lines A549 (human breast cancer) and P-388 (mouse leukemia). $IC_{50}$'s were measured in a colorimetric assay for cytotoxic activity against cultured cells according to the protocol described below:

A three day microtiter assay was used to measure the growth inhibition of cultured cells exposed to a range of drug concentrations. Metabolic activity was measured by the cells' ability to reduce the tetrazolium dye, MTT (3-(4,5-dimethyl-thiazol-2-yl-2,5-diphenyltetrazolium bromide) to a quantifiable colored end product, which absorbs at 570 nm in the visible spectrum. Surviving cells reduce the MTT dye.

Test compounds were dissolved in dimethyl sulfoxide (DMSO) and diluted, first with Earle's Balanced Salt Solution, followed by culture medium, to twice the highest concentration of compound to be tested. From this concentrated stock, two-fold serial dilutions were prepared in 96-well microtiter trays, each well containing twice the desired final concentration of compound. Each concentration was tested in triplicate and compared to triplicate drug-free controls.

The cells were grown in the same medium used for diluting the compounds and then harvested using trypsinization. This involved removing the medium by aspiration; rinsing the cell monolayer twice with Earle's Balanced Salt Solution; adding trypsin (0.05%)/EDTA (0.53 mM; for each 25 $cm^2$, approximately 0.2 mL), tilting to cover the monolayer, and then withdrawing trypsin leaving only a thin film of solution; incubating at room temperature until the cell monolayers detached (as determined by visual and/or microscopic observation); adding medium containing fetal calf serum to stop the action of the trypsin and resuspend the cells; triturating to aid dissociation of cell clumps; and determining the number of cells per milliliter by electronic cell counter (e.g Coulter Counter) or by mixing an aliquot of cell suspension with Trypan Blue (0.4% in normal saline) and counting the viable cells using a hemacytometer.

After harvesting and determination of viable cell counts, cell density was adjusted to 25,000 cells/mL. Inoculum (0.1 mL) containing the cells was then added to each well for a final concentration of 2,500 cells per well. Addition of the inoculum diluted the test compounds to the desired final concentration.

Microtiter trays were then incubated for three days at 36° C. in a humidified atmosphere containing 5% carbon dioxide. After three days, 20 microtiters of 5 mg/mL MTT in phosphate-buffered saline solution were added to each well. Trays were returned to the incubator for two to four hours to allow the surviving cells to reduce the dye. Medium and unreduced dye were removed by aspiration. DMSO was added to each well to dissolve the water-insoluble, colored end product of the dye reduction so that it could be measured spectrophotometrically at 570 nm. The $IC_{50}$ was determined as the concentration of compound tested required to reduce the absorbance at 570 nm to 50% of non-drug treated control values.

The results of testing, shown in Table 3, below, demonstrate the cytotoxic activity of the compounds of the present invention.

TABLE 3

| | In vitro tumor cell cytotoxicity ($IC_{50}$ μg/mL) | | | |
|---|---|---|---|---|
| | A549 | HT-29 | B16F10 | P388 |
| Sample | $IC_{50}$ (μg/mL) | $IC_{50}$ (μg/mL) | $IC_{50}$ (μg/mL) | $IC_{50}$ (μg/mL) |
| Example 5 | 0.003 | 0.0022 | 0.0018 | 0.0055 |
| Example 9 | 0.0045 | 0.0045 | 0.0047 | 0.009 |
| Example 13 | 0.033 | 0.03 | 0.031 | 0.057 |
| Taxol | 0.0027 | 0.0013 | 0.0035 | 0.0077 |

It is understood that the foregoing detailed description and accompanying examples are merely illustrative and are not to be taken as limitations upon the scope of the invention, which is defined solely by the appended claims and their equivalents. Various changes and modifications to the disclosed embodiments, which will be apparent to those skilled in the art, may be made without departing from the spirit and scope of the present invention.

What is claimed is:

1. A compound having the formula

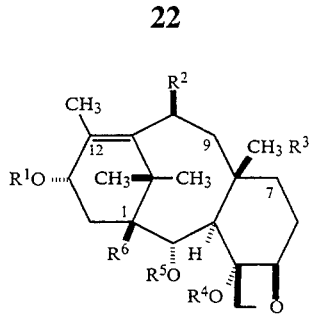

or a prodrug thereof, wherein
$R^1$ is alkanoyl or a radical having the formula

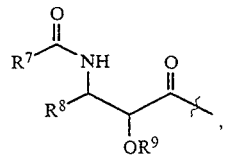

in which $R^7$ is selected from the group consisting of hydrogen, alkyl, phenyl, substituted phenyl, alkoxy, substituted alkoxy, amino, substituted amino, phenoxy and substituted phenoxy; $R^8$ is selected from the group consisting of hydrogen, alkyl, hydroxyalkyl, alkoxyalkyl, aminoalkyl, phenyl, substituted phenyl, α-naphthyl, and β-naphthyl, and $R^9$ is selected from the group consisting of hydrogen, alkanoyl, substituted alkanoyl and aminoalkanoyl;

$R^2$, $R^3$ and $R^6$ are independently selected from the group consisting of hydrogen, hydroxy, alkoxy, aminoalkanoyl and alkanoyloxy;

$R^4$ is selected from the group consisting of alkyl, alkanoyl, aminoalkanoyl and aroyl; and $R^5$ is selected from the group consisting of alkyl, alkanoyl, aminoalkanoyl and aroyl.

2. A compound according to claim 1 wherein $R^1$ is a radical having the formula

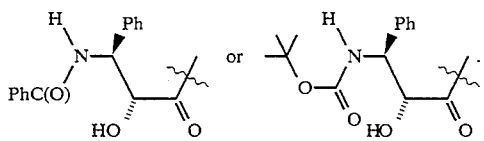

3. A compound according to claim 1 wherein $R^2$ is hydrogen.
4. A compound according to claim 2 wherein $R^2$ is hydrogen.
5. A compound according to claim 1 wherein $R^3$ is hydrogen.
6. A compound according to claim 2 wherein $R^3$ is hydrogen.
7. A compound according to claim 1 wherein $R^2$ and $R^3$ are both hydrogen.
8. A compound according to claim 2 wherein $R^2$ and $R^3$ are both hydrogen.
9. A compound according to claim 1 wherein $R^1$ and $R^4$ are acetyl, $R^2$ is acetoxy, and $R^5$ is hydroxy.
10. A compound according to claim 1 selected from the group consisting of:
13-Acetyl-9-deoxobaccatin III;
9-Deoxotaxol;
13-Acetyl-7-deoxy-9-deoxobaccatin III;
7-Deoxy-9-deoxotaxol;
13-Acetyl-10-desacetoxy-7-deoxy-9-deoxobaccatin III; and
10-Desacetoxy-7-deoxy-9-deoxotaxol.

* * * * *